United States Patent [19]

Friedman-Kien et al.

[11] Patent Number: 5,122,446
[45] Date of Patent: Jun. 16, 1992

[54] METHOD FOR DETECTING ANTIBODIES TO HUMAN IMMUNODEFICIENCY VIRUS

[75] Inventors: Alvin Friedman-Kien; Cao Yunzhen, both of New York; William Borkowsky, Brooklyn, all of N.Y.

[73] Assignee: New York University, New York, N.Y.

[21] Appl. No.: 204,871

[22] Filed: Jun. 10, 1988

Related U.S. Application Data

[63] Continuation-in-part of Ser. No. 40,013, Apr. 17, 1987, Pat. No. 4,865,966.

[51] Int. Cl.$^5$ ................................... G01N 33/569
[52] U.S. Cl. ....................... 435/5; 435/7.92; 435/7.93; 435/7.94; 435/7.95; 435/974; 435/975; 436/501; 436/513; 436/808; 436/811
[58] Field of Search ............. 435/5, 7, 810, 7.92–7.95, 435/974, 975; 436/501, 513, 808, 811

[56] References Cited

U.S. PATENT DOCUMENTS

| | | | |
|---|---|---|---|
| 4,560,647 | 12/1985 | Stocker | 435/5 |
| 4,725,669 | 2/1988 | Essex et al. | 530/395 |
| 4,865,966 | 9/1989 | Friedman-Kien et al. | 435/5 |

FOREIGN PATENT DOCUMENTS

| | | | |
|---|---|---|---|
| 0132170 | 1/1985 | European Pat. Off. | |
| WO86/02930 | 5/1986 | World Int. Prop. O. | 435/5 |
| 88/07680 | 10/1988 | World Int. Prop. O. | 435/5 |

OTHER PUBLICATIONS

Journal of Clinical Investigation, vol. 41, No. 4, 1962, pp. 805–815, M. Lerner et al., "Neutralizing Antibody to Polioviruses in Normal Human Urine".
Chemical Abstracts, vol. 77, Sep. 22, 1977, Abstract No. 86578.
Blood, vol. 67, No. 3, 1986, pp. 831–834, New York, D. W. Archibald et al., "Antibodies to Human T-Lymphotropic Virus Type III (HTLV-III) in Saliva of Acquired Immunodeficiency Syndrome (AIDS) Patients and in Persons at Risk for AIDS".
Clinica Chimica Acta, vol. 139, 1984, pp. 113–117, T. R. Trinick et al., "Measurement of Urinary Immunoglobulins G, A and M by an Enzyme Linked Immunosorbent Assay (ELISA)".
Lancet, Apr. 9, 1988, pp. 831, 832, Cao et al., "IGG Antibodies to HIV-1 in Urine of HIV-1 Seropositive Individuals".
AIDS Research and Human Retroviruses, vol. 5, No. 3, 1989, pp. 311–320, New York, Y. Cao et al., "Antibodies to Human Immunodeficiency Virus Type 1 in the Urine Specimens of HIV-1-Seropositive Individuals".
Lerner et al., "Neutralizing Antibody to Poliovirus in Normal Human Urine", Virology, (1961), 14:383–5.
Meryhew, N. L. et al., J. Rheumat., 10:913–919, 1983.
Takayanagi et al., Clinicopathological Significance of the Analysis of Urinary Antibody Activatives, Rinsho Byroi, *The Japanese Journal of Clinical Pathology,* vol. 22 (Suppl.), Oct., 1974, p. 184, (English Translation).
Bulletino Dell'Istituto Sieriterapico Milanese, vol. 51, No. 1, 1972, pp. 90–102, D. DeDonate et al., "Sugli Anticorpi Antivirali Delle Urine", (*Chemical Abstracts,* vol. 77, Sep. 22, 1977, Abstract No. 86578).

*Primary Examiner*—Christine Nucker
*Attorney, Agent, or Firm*—Darby & Darby

[57] ABSTRACT

Disclosed herein is a method of screening mammals for antibodies to viral agents by collecting a urine sample from a mammal to be tested and assaying the sample for antibodies directed against the specific viral agent.

13 Claims, 2 Drawing Sheets

METHOD FOR DETECTING ANTIBODIES TO HUMAN IMMUNODEFICIENCY VIRUS

BACKGROUND OF THE INVENTION

This application is a continuation-in-part application of co-pending U.S. patent application Ser. No. 040,013 filed Apr. 17, 1987 of Friedman-Kien et al now U.S. Pat. No. 4,865,956.

The present invention relates to a method for detecting antibodies directed against Human Immunodeficiency Virus which can be used for diagnosing AIDS and related diseases, and identifying latent, asymptomatic carriers of such infections.

Acquired Immune Deficiency Syndrome (AIDS) was initially recognized and reported in 1981. Since that time, clinical and epidemiological data have revealed that the incidence of AIDS has reached epidemic levels throughout the world. The causative agent of AIDS has been identified as an RNA retrovirus, the Human T-Cell Leukemia Virus Type III (HTLV-III), also known as Lymphadenopathy Associated Virus (LAV) and AIDS-associated retrovirus (ARV) and recently renamed Human Immunodeficiency Virus (HIV). AIDS patients may suffer from a broad spectrum of opportunistic infections such as Pneumocystis carinii, Candida albicans, herpes simplex virus and cytomegalovirus, and are also frequently afflicted with certain tumors, especially Kaposi's Sarcoma. It has been estimated that the number of patients with AIDS in the United States continues to double approximately every twelve months.

The putative AIDS virus, HIV, has been isolated from peripheral blood mononuclear cells, cerebrospinal fluid, semen, neural tissue, saliva, tears and rarely, urine. In order to determine the prevalence of HIV in the general population, it has been suggested that mass screenings of the population for the presence of antibodies directed against the AIDS virus be undertaken. However, since antibody substances are generally found only in human blood and serum, the proposed screening techniques involve obtaining a blood or serum sample from the patient who is to be screened.

A variety of serological tests have been developed to detect the presence of antibodies to HIV (indicative of exposure to HIV) in the blood of patients with AIDS, AIDS-Related Complex (ARC) and healthy (i.e. asymptomatic) virus carriers. FDA-approved ELISA (enzyme-linked immunosorbent assay), as well as experimental Western Blot kits for the measurement of antibodies against HIV are now available. These include recent (but still experimental) ELISA assay kits that detect specific antibodies directed against the viral envelope protein (gp41 or ENV) and a viral core protein (p24 or CORE) as well as kits utilizing Western Blot technology for detecting the major antigenic proteins of HIV. In addition, methods have been recently developed for detecting these viral antigens in tissue culture fluids of HIV-infected cells cultured in vitro as well.

All of the current AIDS detection methods employ invasive procedures to obtain a blood or serum sample to be analyzed for the presence of antibodies to the HIV virus, i.e. the insertion of a hollow needle or other means for withdrawing a fluid sample from a vein, artery or subcutaneous space. These procedures involve some degree of risk to the health care personnel who are involved in collecting and analyzing these samples as Acquired Immune Deficiency Syndrome may possibly be contracted through inadvertent exposure to a syringe or needle that has been employed to obtain a blood or serum sample from a patient that is afflicted with the disease. Moreover, individuals who are presently considered to be at a high risk of contacting AIDS, such as homosexual men and intravenous drug users, and non-high risk individuals who should be screened, often have unfounded fears that they can contract the disease while being tested for it, and therefore avoid exposure to any test procedures which involve withdrawing blood or serum using a needle.

These problems would be overcome by a non-invasive method for screening for antibodies to HIV. Such a method should be suitable for use in mass screenings and avoid the inherent drawbacks of the prior art invasive serological techniques.

SUMMARY OF THE INVENTION

It has now been unexpectedly discovered that antibodies to HIV can be detected in the urine of patients that have been exposed to, or infected with, HIV. This is a particularly surprising discovery since heretofore it was believed that antibodies could not be detected in human urine except in certain individuals suffering from renal disease. The present invention discloses a non-invasive method for determining whether a patient is infected with HIV virus by detecting the presence of antibodies directed against HIV in the urine of a patient to be screened for HIV.

It is therefore an object of the present invention to provide a non-invasive method for screening for antibodies directed against infectious agents.

In another aspect, the present invention provides a non-invasive method for determining whether an individual has been exposed to a specific viral agent. The method comprises detecting the presence of antibodies directed against the specific viral agent in the urine of a patient who has not been immunized against the specific viral agent.

These and other aspects of the present invention will be apparent to those of ordinary skill in the art in light of the present description, accompanying claims and appended drawings.

DETAILED DESCRIPTION OF THE INVENTION

It has now been unexpectedly discovered that antibodies to the AIDS virus (HIV) are present in the urine of AIDS-patients and HIV-infected individuals, including individuals that are not suffering from renal disorders. In addition, the present inventors have directly identified these HIV antibodies as being members of the IgG and IgA classes of immunoglobulins by immunodiffusion techniques. This discovery is surprising because the prior art suggests that meaningful titers of antiviral antibodies are only present in the urine of patients afflicted with kidney disease, or those who have been immunized by vaccination with the poliovirus vaccine.

Franklin, E. C. (*J. Clin. Invest.* 38:2159–2167, 1959) has disclosed that proteins, including albumin, alpha, beta and gamma globulins, were present in the concentrated urine of normal humans. However, these fragments were only one sixth the size of mature immunoglobulins and were thought to be natural breakdown products of antibody molecules. Specific antibodies were not examined.

An article by Lerner, A. M. et al (*J. Clin. Invest.* 41: 805–815, 1962) discloses that antibodies to poliovirus could be detected in the urine of normal individuals who had been immunized with poliovirus vaccine. However, all of the individuals with detectable urine antibodies had received at least 3 or more inoculations with the vaccine, and urines were analyzed shortly thereafter. The presence of antiviral antibodies in the urine of non-immunized individuals has not been previously reported in the literature. Indeed, the present inventors were unable to detect antibodies directed against cytomegalovirus (CMV) or hepatitis virus in the urine of individuals known to be infected with such viral agents. In the case of CMV, AIDS patients with serum titers of 1:1500 to 1:20,000 of anti-CMV antibodies did not have detectable anti-CMV urinary antibodies, as assayed by ELISA.

Intact antibodies (or fragments of antibodies) directed against HIV present in the urine of infected individuals have not heretofore been reported in the literature. Urinary antibodies are usually found only in non-immunized patients suffering from diseases of the kidney and/or liver such as nephrotic syndrome, glomerulonephritis, hepatorenal syndrome or from those afflicted with multiple myeloma, an immunoproliferative disorder.

The amount of HIV antibodies present in the urine is approximately 20 fold lower than that found in serum, and is often below the limits of detection of currently available diagnostic techniques. Therefore, the urine must be concentrated, i.e. its volume is preferably be reduced relative to its initial void volume, before assaying for such antibodies. More sensitive methods of antibody detection such as those of Example 5, permit the urine concentration step to be eliminated.

The method of the present invention comprises obtaining a urine sample voided by a patient to be screened for exposure to HIV, optionally concentrating the urine sample by reducing the volume of such sample at least about 20 fold in relation to its initial (void) volume, and assaying the concentrated or unconcentrated sample as the casing for the presence of antibodies to HIV. The assay is conducted using techniques that are well-known for detecting the presence of such antibodies in serum. Although as little as 1–5 ml of urine could be examined for the presence of the antibodies sought to be detected, using most currently available methods for antibody detection, 40–100 mls of urine are desirably recovered from the patient to be tested and used in the assay procedure. The urine can be used immediately, stored for 24 hours or longer at 4° C. before use and can be frozen (but deteriorates upon multiple freezing and thawing).

If it is determined that concentration of urine is desired, any of the numerous methods that are well known to those skilled in the art can be used to concentrate (reduce the volume) of the urine sample to be analyzed. Examples of techniques which can be used in practicing the method of the present invention include, but are not limited to, air evaporation, membrane dialysis, rotary evaporation, and preferably using a Minicon B15 concentrator (Amicon, Danvers, MA) with a 60,000 dalton membrane filter as detailed in Example 1 below. Urine can also be concentrated by lyophilization, but this requires larger volumes (e.g. at least 200 ml).

Once the urine sample has been substantially concentrated, it can be assayed for the presence of antibodies to HIV. As used herein with respect to urine volume reduction, substantially concentrated means a volume reduction of at least 20 fold in relation to the initial (void) urine volume, and preferably between about 40 fold and 200 fold with respect to urine volume reduction, i.e. a reduction in volume from an initial (void) volume of 40 ml to a final volume of 2 ml is a 20 fold reduction. The samples can also be lyophilized and resuspended (in, for example isotonic saline) in any volume desired, but as mentioned above, this requires larger volumes.

The sample can be assayed for antibodies to HIV proteins using standard antibody detection techniques including by way of non-limiting example, ELISA, Western Blotting, radio-immunoassay, and immunodiffusion.

In a preferred embodiment of the present invention, the well-known Western Blot Analysis method is employed for anti-HIV antibody detection. This technique has been found to be the most reliable currently available method for detecting HIV antibodies in the urine of mammals. The technique generally comprises separating proteins (in this case, HIV proteins) by gel electrophoresis on the basis of molecular weight, transferring the separated proteins to a suitable solid support, (such as a nitrocellulose filter or alternatively, a nylon filter), and incubating the serum (or urine) of an HIV-infected individual with the separated proteins. This causes specific HIV antibodies present in the serum (or urine) to bind to their respective proteins. HIV antibodies are then detected using labeled anti-human HIV antibodies. This method of detecting antibodies to HIV is preferred due to its sensitivity and the fact that specific antibodies to viral proteins are examined. The incidence of false positive results which are inherent when employing ELISA assays is substantially reduced by using Western Blot Analysis.

An alternative embodiment of the present invention utilizes on Enzyme Linked Immunosorbent Assay (ELISA) as a means for detecting antibodies specific for HIV. ELISA assays for the detection of antibodies to the HIV virus can either be competitive or non-competitive (as described by E. Engvall in *Methods in Enzymology.* 70: 419439, incorporated herein by reference).

ELISA's are immunoassays used (in this case) to quantitate the amount of antibodies present in a sample to be analyzed. The assays employ a chromogen (a color producing substance) for detecting the antibody: antigen complex formed. Antibodies used in ELISA are covalently coupled to these chromogens, such as ortho-phenylenediamine or orthodianisidine, the former producing a tangerine-colored product in the presence of a peroxide (such as hydrogen peroxide) and the latter a yellow-orange colored product in the presence of a peroxide. These colors absorb light at specific wavelengths (ortho-phenylenediamine at 492nm and orthodianisidine at 400nm) and are detected and quantitated using a spectrophotometer.

Non-competitive ELISA tests employ an immobilized antigen in order to capture any antibodies and an enzyme-labeled second antibody directed against the species in which the test antibody has been elicited. If for example, human antibodies are being measured, then goat or rabbit anti-human antibodies are the labeled, second antibody. The amount of antibody present is directly proportional to the amount of bound, labeled second antibody. Competitive ELISA's comprise a reaction in which unlabeled (the biological sample to be tested) and enzyme-labeled antibodies compete for a limited, known amount of antigen. In this case, the reaction is performed until equilibrium is reached, and the concentration of unknown antibody is inversely proportional to the amount of bound, enzyme-labeled antibodies. For example, if there are no antibodies in the unknown sample, all of the labeled antibodies will bind to the antigen, and a high value, indicated by an increased color, will be obtained when measuring the amount of enzyme label present.

Commercially-available ELISA assay kits which can be used in practicing the alternative embodiment of the present invention are available from Abbott Labs (Chicago, Ill.) under Catalog Number 1037 and as ENVACOR (Human T Cell Lymphotropic Virus III, EIA, Catalogue No. 2791-22, Abbott International Diagnostics, Weisbaden, West Germany). The 1037 assay utilizes a non-competitive ELISA (as described in Example 3 below) whereas the ENVACOR test uses a competitive ELISA (as described in Example 2 below). These kits contain the components listed in Examples 2 and 3 below and are offered for use in assaying serum (not urine) for antibodies to HIV.

One important advantage of the method of the present invention is that the biological sample to be analyzed (urine) can be easily obtained by non-invasive techniques, and therefore, the risk of transmitting an HIV infection to laboratory and health care personnel (e.g. through accidental puncture with a contaminated needle) is essentially eliminated.

The method of the present invention can be carried out rapidly. In cases where the urine is concentrated, the speed of carrying out the method of the present invention limited only by the time it takes to concentrate the urine sample to be tested. In broad terms, this can be done in a period of time of less than 90 minutes, when the samples are to be concentrated 200 fold. Concentrating the urine 20–40 fold can be accomplished in less than 60 minutes. The sample can then be analyzed using the commercially-available HIV Serum testing kits.

The invention is described further below in specific working examples which are intended to illustrate the invention without limiting its scope.

EXAMPLE 1

Urine Concentration

Serum samples and 60–100 ml of urine were collected (and numerically coded for patient confidentiality) from the following groups of patients: 28 AIDS-associated Kaposi's sarcoma (AIDS-KS) patients; 21 ARC patients; 48 asymptomatic HIV-infected high risk individuals including (37 homosexual men, 5 female intravenous drug users and 1 female transfusion recipient); and 16 patients suffering from AIDS-related opportunistic infections (AIDS-OI), such as *Pneumocystis Carinii* and cytomegalovirus (Table I contains specific patient identification and assay results) In addition, 17 non-AIDS disease patients' urine and serum, including patients diagnosed as having cirrhosis and hepatoma (1), hepatitis (3), Lupus (3), glomerulonephritis (3), nephrotic syndrome (1), Lupus-nephritis (1), heart failure (1), Lepromatous leprosy (1), tuberculosis (2) and DM nephropathy (1), plus samples from 30 apparently normal, healthy heterosexuals were obtained. The urine samples obtained from all of the normal controls and AIDS patients' displayed essentially normal values for proteins, when assayed using standard urinalysis techniques well known in the art. Proteinuria (the presence of abnormally high concentrations of protein in the urine) is routinely detected using a "dipstick" that registers the presence of high (over 150 mg) concentrations of urinary protein. This is indicated by a color change on the dipstick, which is then compared to standards for quantitation.

The collected urine specimens were centrifuged in conical tubes at 1500 RPM for 15 minutes at room temperature. The supernatant was decanted and saved and the pellet was discarded.

The supernatant obtained above was concentrated between 20 and 200 fold in relation to the volume of initial urine sample collected from the subject to be tested using a Minicon B15 concentrator with a 60,000 dalton membrane (Amicon, Danvers, MA). The concentrator operates by retaining any substance greater than 60,000 daltons molecular weight on the membrane filter, while the solution is evaporated. This takes approximately one hour. (To concentrate the urinary volume 200 times (200×) from an initial or starting volume i.e. to 1/200 of its starting volume using the Mincon apparatus takes approximately 90 minutes). The concentrated urine sample can be stored at 4oC for up to 30 days before use, or used immediately for assay as detailed in Examples 2–5 below. For Western Blot analysis or immunodiffusion studies, sample volumes are preferably further concentrated 200 fold i.e. to 1/200 of the starting volume. The amount each sample was concentrated is listed in Tables 1, 2 and 4 below.

EXAMPLE 2

Elisa Assay of Concentrated Urine Samples

The serum and concentrated urine samples collected in Example I were assayed for the presence of antibodies to ENV and CORE HIV antigens as described (Allain, J. P. et al, *Lancet* I: 1233–1236, 1986, incorporated by reference) using an Abbott Envacore assay kit. This is a competitive ELISA in which known amounts of HIV proteins and antibodies are added together with the sample to be tested. The presence of antibodies in the sample is indicated by a reduction in the binding of the control antisera with the control antibody. The manufacturer's instructions were followed exactly as provided. In addition, blood samples were collected and analyzed simultaneously.

The kit contains a specimen diluent (containing bovine and goat sera and 0.1% sodium azide), enzyme-conjugated polyclonal antibody to HIV envelope and core proteins, beads coated with recombinant gp41 or gp24 HIV proteins, orthophenylenediamene (OPD) substrate, a positive and a negative HIV antibody control and instructions for use.

Fifty microliters of the specimen to be tested, or control, were incubated with 20 microliters of diluent supplied by the manufacturer and 200 microliters of enzyme-conjugated polyclonal human antibody to HIV envelope or core proteins. Beads coated with recombinant gp41 or p24 HIV proteins were added to separate wells containing either the HIV ENV or CORE antibodies. After 16 to 22 hours incubation at room temperature, the beads were washed and transferred to appropriate reaction tubes. Three hundred microliters of ortho-phenylenediamine substrate was then added to each tube and the reaction allowed to proceed for 30 minutes before addition of 1 ml 1N $H_2SO_4$ to stop the reaction. Absorbance values of the solution were measured at 492 nm using a spectrophotometer sold by Abbott Labs under the name Quantum II, number 3303-11. A positive result for the presence of urine or serum antibodies to either the HIV p24 or gp41 proteins was defined as any specimen with absorbance values equal to or less than 0.5 times the sum of the optical density (O.D.) of mean negative control (provided by the manufacturer) optical density (O.D.) plus the O.D. of the mean positive control (provided by the manufacturer) as measured in above.

A tabular identification of the patients screened with the present invention and the assay results are presented in Tables 1 and 2 and summarized in Table 3.

TABLE 1

The Antibodies to HIV in the serum and urine of AIDS-KS, AIDS-OI, ARC groups, and HR groups

| Patient Number | Sex | Code | Concentration | Presence in Serum of ENV | Presence in Serum of Core | Presence in Urine of ENV | Presence in Urine of Core |
|---|---|---|---|---|---|---|---|
| AIDS-KS | | | | | | | |
| 1 | M | 1029 | 47 × | + | + | + | − |
| 2 | M | 993 | 100 × | + | + | − | − |
| 3 | M | 716 | 42 × | + | − | + | − |
| 4 | M | 818 | 33 × | + | − | + | − |
| 5 | M | 871 | 67 × | + | + | + | − |
| 6 | M | 894 | 33 × | + | + | + | − |
| 7 | M | 953 | 40 × | + | − | + | − |
| 8 | M | 5009 | 34 × | + | + | + | − |
| 9 | M | 5018 | 45 × | + | − | + | − |
| 10 | M | 5057 | 39 × | + | + | + | − |
| 11 | M | 5062 | 42 × | + | + | − | − |
| 12 | M | 1028 | 48 × | − | + | + | − |
| 13 | M | 828 | 42 × | + | + | + | − |
| 14 | M | 5061 | 37 × | + | − | + | − |
| 15 | M | 5059 | 35 × | + | − | − | − |
| 16 | M | 276 | 20 × | + | + | + | − |
| 17 | M | 1056 | 40 ×−200 × | + | + | − | − |
| 18 | M | 5098 | 40 × | + | + | − | − |
| 19 | M | 5013 | 35−200 × | + | − | − | − |
| 20 | M | 5050 | 20 × | + | + | + | − |
| 21 | M | 5074 | 42 × | + | − | − | − |
| 22 | M | 5080 | 42 × | + | + | − | − |
| 23 | M | 5051 | 40 × | + | + | − | − |
| 24 | M | 5083 | 41 × | + | − | + | − |
| 25 | M | 5097 | 40 × | + | − | + | − |
| 26 | M | 1083 | 42 × | + | − | + | − |
| 27 | M | 1081 | 40 × | + | − | − | − |
| 28 | M | 1084 | 40 × | + | + | − | − |
| ARC Patients | | | | | | | |
| 29 | M | 1022 | 56−200 × | + | + | − | − |
| 30 | M | 857 | 62−200 × | + | + | − | − |
| 31 | M | 920 | 47 × | + | − | + | − |
| 32 | M | 598 | 35 × | + | + | − | − |
| 33 | M | 1002 | 40 × | + | + | + | − |
| 34 | M | 1015 | 35 × | + | − | + | − |
| 35 | M | 1016 | 35 × | + | + | − | − |
| 36 | M | 1021 | 50 × | + | + | + | − |
| 37 | M | 949 | 40 × | + | + | + | − |
| 38 | M | 901 | 100 × | + | − | + | − |
| 39 | M | 898 | 100 × | + | − | + | − |
| 40 | M | 956 | 100 × | + | + | + | − |
| 41 | M | 839 | 47 × | + | − | + | − |
| 42 | M | 1039 | 41 × | + | − | + | − |
| 43 | M | HEN03 | 41 × | + | − | + | − |
| 44 | M | HEN04 | 42 × | + | − | + | − |
| 45 | M | HEN05 | 42 × | + | − | + | − |
| 46 | M | HEN06 | 42 × | + | − | + | − |
| 47 | M | HEN07 | 41 × | + | − | + | − |
| 48 | M | HEN08 | 42 × | + | + | + | − |
| 49 | M | HEN09 | 40 × | + | + | + | − |

ENV = Antibody to HIV envelope [anti-env (gp41)]
Core = Antibody to HIV core [anti-gag (p24)]

TABLE 2

Antibodies to HIV in the serum and urine of the High-Risk group and AIDS-OI

| Patient Number | Sex | Code | Fold Concentration | Serum ENV | Serum Core | Urine ENV | Urine Core |
|---|---|---|---|---|---|---|---|
| HIGH-RISK | | | | | | | |
| 50 | M | 1024 | 37−200 × | + | − | − | − |

TABLE 2-continued
Antibodies to HIV in the serum and urine of the High-Risk group and AIDS-OI

| Patient Number | Sex | Code | Fold Concentration | Serum ENV | Serum Core | Urine ENV | Urine Core |
|---|---|---|---|---|---|---|---|
| 51 | M | 1060 | 30 × | + | − | − | − |
| 52 | M | 1059 | 32 × | − | − | − | − |
| 53 | M | 1062 | 40 × | + | − | − | − |
| 54 | M | 1057 | 28 × | + | + | + | − |
| 55 | M | 1055 | 32 × | − | − | − | − |
| 56 | M | 1058 | 40 × | + | + | + | − |
| 57 | M | 1052 | 37 × | − | − | − | − |
| 58 | M | A$_2$-014 | 50 × | + | + | + | − |
| 59 | M | A$_1$-078 | 33 × | + | + | + | − |
| 60 | M | 0697550 | 40 × | + | − | + | − |
| 61 | M | 0820835 | 44 × | + | + | + | − |
| 62 | M | 1061 | 41 × | + | + | + | − |
| 63 | M | A$_1$-029 | 40 × | + | + | − | − |
| 64 | M | A$_1$-136 | 41 × | + | + | − | − |
| 65 | M | A$_1$-138 | 39 × | + | − | − | − |
| 66 | M | A$_1$-044 | 41 × | + | + | + | − |
| 67 | M | A$_1$-045 | 40 × | + | + | + | − |
| 68 | M | A$_1$-173 | 42 × | + | + | + | − |
| 69 | M | A$_1$-003 | 42 × | + | + | + | + |
| 70 | F | 1065754 | 40 × | + | + | + | − |
| 71 | M | 0471024 | 40 × | + | + | + | − |
| 72 | M | A$_2$-132 | 40 × | + | + | + | − |
| 73 | M | A$_2$-115 | 40 × | + | + | + | + |
| 74 | M | A$_1$-060 | 40 × | + | + | − | − |
| 75 | M | A$_1$-178 | 43 × | + | + | − | − |
| 76 | M | A$_2$-090 | 40 × | + | + | + | − |
| 77 | M | A$_2$-097 | 40 × | + | + | + | − |
| 78 | M | A$_2$-137 | 40 × | + | + | + | − |
| 79 | F | U16 | 41 × | + | − | + | + |
| 80 | M | 1091 | 42 × | − | − | − | − |
| 81 | M | 1093 | 42 × | + | + | + | − |
| 82 | M | 1110 | 42 × | + | + | + | − |
| 83 | M | 1121 | 40 × | + | − | + | − |
| 84 | M | 1080 | 41 × | − | − | − | − |
| 85 | M | 1070 | 40 × | + | − | + | − |
| 86 | M | 1111 | 40 × | + | + | − | − |
| 87 | M | 1107 | 40 × | + | + | + | + |
| 88 | M | 1116 | 49 × | + | + | + | + |
| 89 | F | 941151 | 46 × | + | − | + | − |
| 90 | M | 1098 | 41 × | + | − | + | − |
| 91 | F | U17 | 40 × | + | − | − | − |
| 92 | F | U19 | 42 × | + | + | + | + |
| 93 | F | U20 | 42 × | + | + | + | − |
| 94 | M | A$_2$-036 | 42 × | + | − | + | − |
| 95 | M | A$_1$-082 | 40 × | + | + | − | − |
| 96 | M | A$_1$-177 | 42 × | + | − | − | − |
| 97 | M | 1073 | 40 × | + | − | − | − |
| PATIENTS WITH OPPORTUNISTIC INFECTIONS | | | | | | | |
| 98 | M | 644 | 40 × | + | + | + | − |
| 99 | M | 1063 | 23 × | + | − | − | − |
| 100 | M | 155 | 43 × | + | + | − | − |
| 101 | M | 156 | 40 × | */ | / | + | − |
| 102 | M | 157 | 40 × | + | + | − | − |
| 103 | M | 1108 | 40 × | + | − | + | − |
| 104 | M | 1112 | 40 × | + | − | − | − |
| 105 | M | 1113 | 42 × | + | + | − | − |
| 106 | M | 159 | 41 × | + | − | + | − |
| 107 | F | 160 | 41 × | + | − | + | − |
| 108 | M | 161 | 40 × | + | + | + | − |
| 109 | F | 162 | 42 × | + | + | + | − |
| 110 | M | 164 | 44 × | + | + | + | − |
| 111 | M | 165 | 40 × | + | − | + | − |
| 112 | M | 166 | 41 × | + | − | + | − |
| 113 | M | 473 | 35 × | + | − | + | − |

* / = not done

TABLE 3
Summary of ELISA assay for HIV ENV antibodies in the Concentrated Urine Samples

| PATIENT TYPE | SERUM/URINE + − | SERUM/URINE + + | SERUM/URINE − − | % SERUM/URINE + + |
|---|---|---|---|---|
| AIDS/KS | 8 | 20 | 0 | 20/28 = 71.4% |
| ARC | 4 | 17 | 0 | 17/21 = 81.0% |
| HIGH RISK | 13 | 30 | 5 | 30/3 = 69.7% |

TABLE 3-continued

Summary of ELISA assay for HIV ENV antibodies in the Concentrated Urine Samples

| PATIENT TYPE | SERUM/URINE + - | SERUM/URINE + + | SERUM/URINE - - | % SERUM/URINE + + |
|---|---|---|---|---|
| OPPORTUNISTIC INFECTION | 5 | 11 | 0 | 11/16 = 68.8% |
| TOTAL | 30 | 78 | 5 | 78/113 = 72.2% |

Referring to Tables 1 and 2, it can be seen that 71.4% of the AIDS-induced Kaposi's sarcoma patients, 81% of the ARC patients, 69.7% of the patients in the high risk group and 68.8% of patients suffering from opportunistic infections had antibodies to the ENV protein (gp41) of HIV present in their urine and that such antibodies were detected using the methods of the present invention. The total percentage of patients with detectable HIV ENV antibodies was 72.2%. The core antigen was only detected in the urine of 6 individuals, those being in the asymptomatic infected high risk group. All of the non-AIDS disease patients and the normal, healthy heterosexuals' urine and serum were negative for antibodies to both HIV proteins.

EXAMPLE 3

A subset of the urine samples analyzed in Example 1 were re-examined using two commercially-available non-competitive HIV ELISA detection kits. KIT I (HTLV III EIA kit, Lot No. 1590HR00, Abbott Laboratories, Chicago, Ill.) is an FDA-approved clinical diagnostic kit., Kit II (EIA Clinical Diagnostic Kit, Catalog No. 1037, Abbott Laboratories, Chicago, IL) is intended for investigative use only.

Each of the kits contain HIV antigen-coated beads, goat anti-human antibody conjugated to horseradish peroxidase, a positive control, a negative control, specimen diluent containing bovine and goat sera, OPD and an OPD diluent containing citrate-phosphate buffer and 0.02% hydrogen peroxide, reactron trays,, assay tubes and instructions for use.

The assay for the presence in the urine of a patient to be tested of antibodies to HIV is performed as follows. 10 microliters of control or diluted specimen is dispensed into preselected wells of the reaction tray. Each well can hold up to 400 microliters of fluid. Two hundred microliters of specimen diluent and one bead are added per well. The reactions are incubated for about 1 hour at 40° C. Thereafter, the supernatant (i.e. liquid) is discarded and the bead washed three times with 4 to 6 ml of distilled or deionized water. Two hundred microliters of labeled goat-anti-human antibodies are then added and incubated at 40° C. for about 2 hours. The supernatant is removed and the bead is washed as above. The bead is transferred to an assay tube, 300 microliters of OPD substrate solution is added, and the solution is incubated for about 30 minutes. 1 ml of IN sulfuric acid is added and the absorbance of the solution determined at 492nm in a standard Abbott Labs spectrophotometer (Model 3303-11 available from Abbott Labs). A positive value is indicated if a sample is within the range of 0.5 to 1.5 times the positive control mean.

The results of these assays are presented below in Table 4.

TABLE 4

| Patient Number | Patent | Fold Concentration | KIT I Urine HIV Antibody | KIT II Urine HIV Envelope Antibody |
|---|---|---|---|---|
| AID-KS | | | | |
| 1 | 1029 | 47 × | + | + |
| 3 | 716 | 42 × | + | + |
| 4 | 818 | 33 × | + | + |
| 5 | 871 | 67 × | − | + |
| 6 | 894 | 33 × | + | + |
| 7 | 953 | 40 × | − | + |
| 8 | 5009 | 34 × | + | + |
| 9 | 5018 | 45 × | − | + |
| 10 | 5057 | 39 × | − | + |
| 11 | 5062 | 42 × | − | − |
| 12 | 1028 | 48 × | + | + |
| 13 | 828 | 42 × | − | + |
| 14 | 5061 | 37 × | + | + |
| 16 | 276 | 20 × | − | + |
| 17 | 1056 | 40 ×-200 × | − | + |
| 19 | 5013 | 35 ×-200 × | − | − |
| 20 | 5050 | 20 × | − | + |
| 21 | 5074 | 42 × | + | + |
| 22 | 5080 | 42 × | − | − |
| ARC | | | | |
| 30 | 857 | 62 ×-200 × | − | + |
| 31 | 920 | 47 × | − | + |
| 32 | 598 | 35 × | − | − |
| 33 | 1002 | 40 × | + | + |
| 34 | 1015 | 35 × | − | + |
| 35 | 1016 | 35 × | − | − |
| 36 | 949 | 40 × | − | + |
| 40 | 956 | 100 × | − | + |
| 41 | 839 | 47 × | − | + |
| HIGH-RISK | | | | |
| 52 | 1059 | 32 × | − | − |
| 53 | 1067 | 40 × | − | − |

TABLE 4-continued

| Patient Number | Patent | Fold Concentration | KIT I Urine HIV Antibody | KIT II Urine HIV Envelope Antibody |
|---|---|---|---|---|
| 54 | 1057 | 28 × | − | + |
| 55 | 1055 | 32 × | − | − |
| 57 | 1052 | 37 × | − | − |
| 58 | A₂-014 | 50 × | − | + |
| 59 | A₁-078 | 33 × | − | + |
| 60 | 0697550 | 40 × | − | + |
| 61 | 0820535 | 44 × | − | + |
| 62 | 1061 | 41 × | − | + |
| 63 | A₁-029 | 40 × | − | − |
| 64 | A₁-136 | 41 × | − | − |
| 65 | A₁-138 | 39 × | − | − |
| 66 | A₁-044 | 41 × | − | + |
| 67 | A₁-045 | 40 × | − | + |
| 68 | A₁-173 | 42 × | − | + |
| 69 | A₁-003 | 42 × | + | + |
| PATIENTS WITH OPPORTUNISTIC INFECTION | | | | |
| 98 | 644 | 40 × | + | + |
| 99 | 1063 | 23 × | − | − |
| 100 | 155 | 43 × | − | − |
| 101 | 156 | 40 × | + | + |
| 102 | 157 | 40 × | − | − |

The results presented in Table 4 demonstrate that urine antibodies to HIV are more readily detectable when employing a more sensitive ELISA assay kit (Kit II). This is the same as for serum antibodies. A limited number of these samples were further analyzed using the Western Blot technique as described below in Example 4.

EXAMPLE 4

Western Blot Analysis of Concentrated Urine Samples

Western Blot analysis for the presence of anitbodies to HIV was performed on the urine and serum samples collected from 59 HIV sero-positive (including 18 AIDS-KS, 27 High Risk individuals, 6 ARC and 8 O.I. patients selected from those reported in Tables 1 and 2 above) and 30 non-AIDS disease patients. A commercially-available kit (Biotech/DuPont HTLV-III Western Blot Kit, available from E. I. DuPont De Nemours and Co., Inc., Wilmington, Del.) was used in making the analysis. The kit contains precut nitrocellulose membrane strips with immobilized viral antigens that have been separated by sodium dodecyl sulfate/polyacrylamide gel electrophoresis (SDS-PAGE) and electroblotted onto the membrane; control sera, including a negative control, a weak positive control and a strong positive control; blotting buffer (Tris buffered saline with 5% nonfat dry milk and also containing heat inactivated normal goat serum); wash buffer (Tris buffered saline containing tween-20 detergent); biotinylated goat anti-human IgG; avidin-horseradish peroxidase; 4-chloro-1-naphthol in solution; hydrogen peroxide; and an incubation tray. The kit was used exactly according to the manufacturer's instructions as described below.

The assay comprises soaking the strips in 2 mls of wash buffer in a well of the wash tray for 30 minutes at room temperature; the liquid is then drained off and discarded. The strips are then washed with 2 mls of blotting buffer for 5–10 minutes at room temperature. Twenty microliters of a 200 fold concentrated urine sample are added to the wells containing the strips and blotting buffer and the reactant incubated overnight at room temperature. Thereafter, the mixture in the wells is aspirated and discarded and the wells are washed once with 2 mls of wash buffer. Two additional 2 ml washes (with wash buffer) are performed at room temperature, allowing 5 minutes soaking between each wash and discarding the wash afterwards.

The nitrocellulose strips are developed as follows. Two mls of biotinylated goat anti-human IgG are added to each well and allowed to incubate for 60 minutes at room temperature on a rocking or rotary apparatus. The strips are then washed with 2 mls of wash buffer per strip for 5 minutes; this step is then repeated 3 additional times at room temperature, discarding the wash after each use. Two mls per strip of avidin-horseradish peroxidase are added and incubated for 60 minutes at room temperature on a rocking or rotary apparatus. The strips are washed 3 times as above. Two mls of a 50:50 mixture of 4-chloro-1-naphthol and hydrogen peroxide are then added and allowed to incubate for 10–15 minutes or until the color develops at room temperature. The presence of color on the strip indicates that the strip has been exposed to a biological fluid (i.e. urine) containing antibodies to HIV.

The strips are scored for the presence of antibodies to HIV as negative (−) i.e. no antibodies to HIV detected, weakly positive (±) or strongly positive (+) using the controls supplied by the manufacturer as references. The results are presented in Table 5 and FIG. 1.

TABLE 5

Results of Western Blot analysis of concentrated urine samples

| Patient Number | Code | p17 | p24 | p31 | p41 | p51 | p55 | p66 | p110/p120 | p160 |
|---|---|---|---|---|---|---|---|---|---|---|
| AID-KS | | | | | | | | | | |
| 1 | 1029 | − | − | − | + | − | − | − | + | + |
| 7 | 953 | − | − | + | ± | − | − | − | + | + |
| 8 | 5009 | − | + | + | − | + | + | − | + | + |

TABLE 5-continued

Results of Western Blot analysis of concentrated urine samples

| Patient Number | Code | p17 | p24 | p31 | p41 | p51 | p55 | p66 | p110/p120 | p160 |
|---|---|---|---|---|---|---|---|---|---|---|
| 9 | 5018 | − | − | + | + | + | − | + | + | + |
| 10 | 5057 | − | + | + | − | + | − | + | + | + |
| 12 | 1028 | − | − | − | + | − | − | − | + | + |
| 13 | 828 | − | − | + | − | + | + | + | + | + |
| 14 | 5061 | − | − | + | ± | − | − | − | + | + |
| 16 | 276 | − | + | + | + | + | + | + | + | + |
| 17 | 1056 | − | − | − | − | ± | ± | ± | + | + |
| 18 | 5098 | − | + | + | − | + | − | + | − | + |
| 21 | 5074 | − | − | + | − | + | − | + | + | − |
| 22 | 5080 | − | − | − | − | − | − | − | − | − |
| 23 | 5051 | − | − | − | − | − | − | − | − | + |
| 24 | 5083 | − | − | − | + | − | − | − | + | + |
| 25 | 5097 | − | + | + | + | + | + | + | + | + |
| 26 | 1083 | − | − | − | − | − | − | − | − | − |
| 27 | 1081 | − | − | − | + | − | + | − | + | + |
| ARC | | | | | | | | | | |
| 33 | 1002 | − | + | + | + | + | + | + | + | + |
| 40 | 956 | − | − | + | + | + | − | + | + | + |
| 42 | 1039 | − | + | + | + | + | + | + | + | + |
| 43 | Hen03 | − | − | − | + | − | − | + | − | − |
| 44 | Hen04 | − | − | + | + | + | − | + | + | + |
| 45 | Hen05 | + | − | + | + | + | + | + | + | + |
| Asymptomatic High-Risk homosexuals | | | | | | | | | | |
| 54 | 1057 | − | + | + | + | − | − | + | + | + |
| 58 | A2-014 | − | ± | − | ± | − | ± | ± | + | + |
| 59 | A1-078 | − | + | + | ± | − | + | + | + | + |
| 60 | 697550 | − | − | + | + | + | + | + | + | + |
| 61 | 820835 | − | + | + | * | + | + | + | + | + |
| 62 | 1061 | − | − | − | − | − | − | − | + | + |
| 66 | A1-044 | − | − | + | − | − | − | − | + | + |
| 67 | A1-045 | − | + | + | + | + | + | + | + | + |
| 68 | A1-173 | + | + | + | + | + | + | + | + | + |
| 69 | A1-003 | + | + | + | + | + | + | + | + | + |
| 70 | 1065754 | + | + | + | + | + | + | + | + | + |
| 71 | 471024 | − | + | − | − | − | + | + | + | + |
| 72 | A2-132 | + | + | + | + | + | + | + | + | + |
| 74 | A1-060 | − | − | − | − | − | − | − | − | + |
| 75 | A1-178 | − | + | + | + | + | + | + | + | + |
| 76 | A2-090 | − | + | − | + | − | + | + | + | + |
| 77 | A2-097 | + | + | + | + | + | + | + | + | + |
| 78 | A2-137 | + | + | + | + | + | + | + | + | + |
| 79 | U16 | + | + | + | + | + | + | + | + | + |
| 81 | 1093 | − | + | − | + | − | + | + | + | + |
| 82 | 1110 | − | + | + | + | + | + | + | + | + |
| 83 | 1121 | − | − | − | * | − | − | − | − | + |
| 85 | 1070 | + | + | − | + | − | + | + | + | + |
| 86 | 1111 | − | * | + | + | + | − | + | − | + |
| 87 | 1107 | + | + | + | + | + | + | + | + | + |
| 88 | 1116 | + | + | + | + | + | + | + | + | + |
| 90 | 1098 | + | + | + | + | + | + | + | + | + |
| Opportunistic Infections | | | | | | | | | | |
| 98 | 644 | − | − | − | − | − | − | − | − | − |
| 99 | 1063 | − | − | − | − | − | − | − | − | − |
| 100 | 156 | − | − | − | + | − | − | − | + | + |
| 102 | 157 | − | * | − | − | − | − | − | − | + |
| 103 | 1108 | + | − | + | + | + | + | + | + | + |
| 104 | 1112 | − | − | − | + | + | − | + | + | + |
| 105 | 1113 | − | − | + | + | + | + | + | + | + |
| 113 | 473 | + | + | + | + | + | + | + | + | + |

* = indeterminate results

TABLE 6

Comparison of Results of Western Blot analysis of concentrated urine and serum samples

| HIV Protein | AIDS-KS Serum | AIDS-KS Urine | ARC Serum | ARC Urine | HIGH-RISK Serum | HIGH-RISK Urine | O.I. Serum | O.I. Urine |
|---|---|---|---|---|---|---|---|---|
| p17 | 18/18* | 1/18 | 2/6 | 1/6 | 26/27 | 11/27 | ⅛ | ⅛ |
| p24 | 18/18 | 5/18 | 6/6 | 2/6 | 25/27 | 23/27 | ⅛ | ⅛ |
| p31 | 18/18 | 9/18 | 6/6 | 5/6 | 26/27 | 19/27 | 8/8 | ⅛ |
| p41 | 18/18 | 11/18 | 6/6 | 6/6 | 26/27 | 23/27 | 8/8 | ⅛ |
| p51 | 18/18 | 8/18 | 6/6 | 5/6 | 27/27 | 16/27 | 8/8 | 4/8 |
| p55 | 18/18 | 7/18 | 6/6 | 3/6 | 27/27 | 21/27 | 8/8 | ⅛ |

TABLE 6-continued

Comparison of Results of Western Blot analysis of concentrated urine and serum samples

| HIV Protein | AIDS-KS Serum | AIDS-KS Urine | ARC Serum | ARC Urine | HIGH-RISK Serum | HIGH-RISK Urine | O.I. Serum | O.I. Urine |
|---|---|---|---|---|---|---|---|---|
| p66 | 18/18 | 7/18 | 6/6 | 6/6 | 27/27 | 23/27 | 8/8 | 4/8 |
| p120 | 18/18 | 15/18 | 6/6 | 5/6 | 27/27 | 24/27 | 8/8 | |
| p160 | 18/18 | 16/18 | 6/6 | 5/6 | 27/27 | 26/27 | 8/8 | 8/8 |

*18 positives per 18 patients tested.

Referring to Table 5, p17 is a protein component produced upon cleavage of p55 to p≧, p≧ is the viral core protein, p31 is the viral endonuclease, p41 is the mature envelope protein, p51 and p66 are components of the viral reverse transcriptase, p55 is a precursor to the viral core protein and p160 is a precursor to the envelope protein; p110/120 is a mixture of 2 proteins which co-migrate in this gel system: p120 is a protein component produced upon processing of the p160 protein to gp41; p110 is a protein component of the virus whose function is currently unknown.

Figure 1:
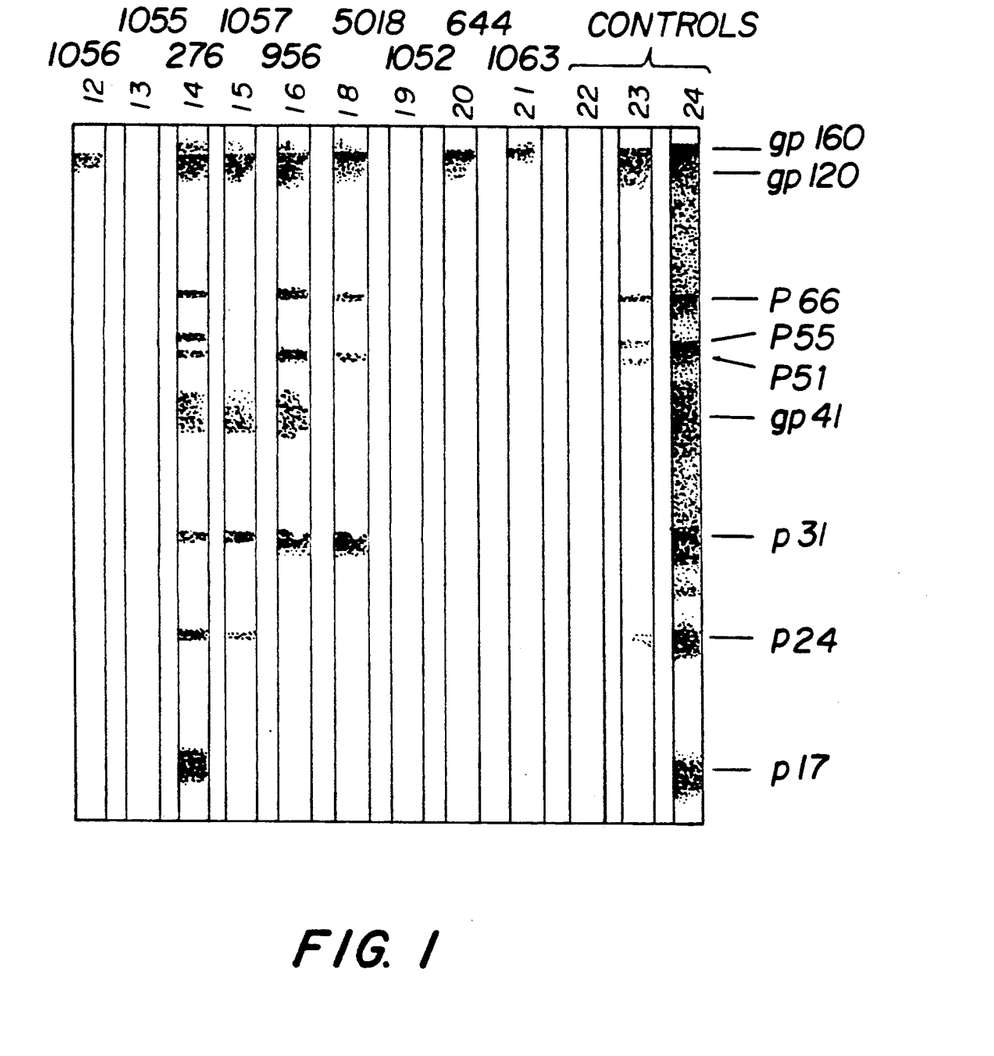
FIG. 1 is a drawing showing a representative Western Blot analysis of the concentrated urine samples of the present invention.

An example of a typical a Western Blot analysis of the concentrated urine and serum samples obtained by practicing the method of the present invention is shown in FIG. 1. Referring to FIG. 1, lane 22 is the negative control, lane 23 the weakly positive control and lane 24 the strong positive control; the numbers to the right represent the various HIV proteins discussed above. Above lines 12–16 and 18–21 are the corresponding patients as referred to in Table 5 above. For example, urine obtained from patient No. 956 (FIG. 1, lane 16), suffering from ARC contained antibodies directed against all of the HIV proteins except p24 (Core) and p17. The significance of this finding is presently unknown.

As can be seen from the data in Table 5 and summarized in Table 6, antibodies to HIV antigens can be readily found (when present) in the concentrated urine samples using this more sensitive technique. In particular, antibodies to p160 in the concentrated urine could be detected in 55 out of the 59 HIV-positive individuals tested (93.2%). These results also demonstrate that the use of concentrated urine in this preferred embodiment of the present invention does not lead to false positives, since specific viral proteins are identified.

EXAMPLE 4

Double-Diffusion Gradient Immunoelectrophoretic Analysis of HIV Antibody-Containing Urine Samples Concentrated urine sample No. 956 (Table I), which tested positive for HIV antigens using Western Blot analyses and antibodies directed against the envelope protein using ELISA, was further concentrated 200 fold and analyzed by double-diffusion gradient immuno-electrophoresis (DDG-IEP) as described by J. V. Chuba. in *J.App. Biochem.*, 1: 37–50, 1979, (incorporated by reference). Serum samples from this patient were collected and analyzed in parallel to the patient urine samples as a positive control.

Briefly, replicate samples of 3 microliters of urine and serum respectively were electrophoresed in commercially prepared 0.5% agarose thin layer gels (Paragon, Beckman Instruments Brea, Calif.). Troughs were placed at right angles to the gels for the addition of antisera. Electrophoresis was performed by subjecting the gels to 20 minutes of direct current on a slightly modified Hyland Power Pack (Costa Mesa, Calif.) at the 40 mA setting. The running buffer contained barbital buffer B-2 (0.075M, pH 8.6; containing 0.2% (w/v) sodium azide) mixed with an equal volume of 3.0 mM aqueous calcium lactate solution.

After electrophoresis, the antisera troughs were completed by removing the corresponding segment of the gel between the precut slits, and conventional parallel-trough immunodiffusion was performed. 7.5 microliters of anti-human IgG, IgM and IgA (Behring Diagnostics, San Diego, CA) at a concentration of 5.5 micrograms per ml was added to the troughs and incubated for 20 minutes at room temperature. Thereafter, the gels were stained and examined for the development of percipitin lines. Anti-albumin antibodies were included in the serum samples as a positive control.

Figure 2:
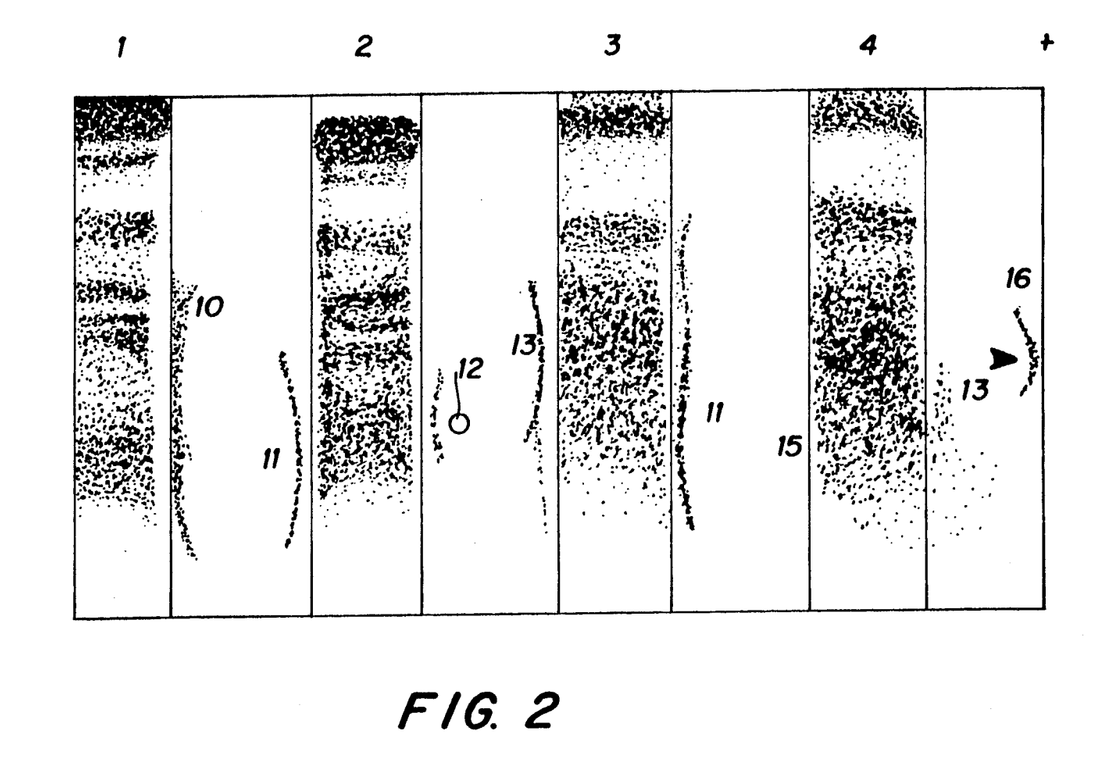
FIG. 2 is a drawing showing a double-diffusion gradient immunometric analysis of HIV antibodies present in the urine of an HIV infected individual.

As shown in FIG. 2, IgG (11) and IgA (13) immunoglobulins were identified in the urine sample of patient No. 956. IgM, although present in the serum did not appear in the urine (12). This is not surprising due to the large size of this immunoglobulin (approximately 900,000 daltons). Anti-albumin antibodies reacted with the serum samples, as expected (10), forming a sharp percipitin line of identity (lane 1). These results confirm the positive results obtained from the ELISA and Western Blot detection procedures, and demonstrate that they were not due to artifacts caused by use of concentrated urine samples.

EXAMPLE 5

Analysis of Unconcentrated Urine Samples for HIV Antibodies by Western Blot and Elisa In Example 4 above, 20 microliters of each concentrated urine sample tested was diluted with 2 ml (i.e. a 1:100 dilution) of the diluted wash buffer provided by the manufacturer before conducting the Western Blot analysis. Using unconcentrated urine, the present inventors have increased this recommended urine volume to be tested to 2 ml and no diluted wash buffer was added. The Western Blot assay was then performed exactly as described in Example 4 above. These samples were then compared with 200-fold concentrated urine samples and serum samples obtained from HIV sero-positive individuals.

For the ELISA assay, the manufacturer's suggested assay procedure, usually used for serum analysis, requires 10 microliters of each serum specimen to be diluted with 200 microliters of the specimen diluent provided in the EIA kit. 10 microliters of this diluted specimen is then further diluted with 200 microliters of the specimen diluent provided in each well. This is a 400-fold dilution of the sample.

The above procedure (designed for serum analysis) was adapted and modified for evaluation of detectable antibodies to HIV in the unconcentrated urine specimens. The recommended first step dilution of the urine specimen with the specimen diluent was eliminated. Instead, the volumes of unconcentrated urine samples tested were increased to 150 microliters, to which 50 microliters of specimen diluent was added. The assay was then performed exactly as described in Example 3 above.

The results of these assays is shown in Table 7.

TABLE 7

Presence of antibodies to HIV-1 antigens in HIV-1 seropositive individuals as determined by ELISA and Western Blot tests.

| Catalogue of Samples | Total # Tested | ELISA No. (%) | Number reactive (%) by Western blot | | | | | | | | |
|---|---|---|---|---|---|---|---|---|---|---|---|
| | | | p17 | p24 | p31 | gp41 | p51 | p55 | p66 | gp120 | gp160 |
| Serum | 100 | 100(100) | 87(87.0) | 96(96.0) | 97(97.0) | 100(100) | 98(98.0) | 99(99.0) | 99(99.0) | 100(100) | 100(100) |
| Conc. Urine 200 × | 100 | 91/91 (100) | 24/87 (27.6) | 51/96 (53.1) | 61/97 (62.9) | 69/100 (69.0) | 57/98 (58.2) | 50/99 (50.5) | 71/99 (71.7) | 96/100 (96.0) | 100/100 (100) |
| Unconc. Urine using *modified procedure | 100 | 93/100 (93.0) | 27/87 (31.0) | 56/96 (58.3) | 67/97 (69.1) | 79/100 (79.0) | 58/98 (58.2) | 48/99 (48.5) | 73/99 (73.7) | 99/100 (99.0) | 100/100 (100) |

*See Method

From the results presented in Table 7 above, it can be seen that unconcentrated urine can be used in both the Western Blot and ELISA assays.

The above invention has been described in terms of preferred embodiments. It would be obvious to those of ordinary skill in the art that many additions, deletions and substitutions could be made without departing from the spirit and scope of the invention, as claimed below.

What is claimed is:

1. A method for identifying the members of a human patient population that have been infected with Human Immunodeficiency Virus (HIV) which comprises:
    contacting a quantity of urine voided by a member of said patient population with an immunoreagent specific for detecting the presence in said urine of an antibody to at least one HIV protein, to form a complex,
    detecting the presence of said complex after said contacting step to obtain a result,
    comparing said result with a standard result which has been obtained by contacting with said immunoreagent urine of at least one human subject known to be free of HIV infection.

2. A method for determining whether a human subject has been infected with Human Immunodeficiency Virus (HIV) comprising the steps of:
    obtaining a urine sample from said human,
    assaying said sample by contacting at least an aliquot of said sample with an immunoreagent specific for detecting the presence of an antibody to at least one HIV protein in said sample to form a complex,
    detecting said complex after said contacting step to obtain a result,
    comparing said result of said assay with those of the same assay performed with urine from at least one HIV-free control human subject.

3. A method for screening a human subject for exposure to Human Immunodeficiency Virus (HIV) comprising the steps of:
    obtaining a urine sample from said subject;
    assaying said sample by contacting at least an aliquot of said sample with an immunoreagent specific for detecting the presence of an antibody to at least one HIV protein to form a complex,
    detecting said complex, and
    determining whether said subject has been exposed to HIV based on the positive presence of at least one antibody of HIV in said sample.

4. A method for detecting the presence of antibodies to Human Immunodeficiency Virus (HIV) in a human subject comprising the steps of:
    obtaining a urine sample from said human subject;
    assaying said sample for the presence of at least one antibody to at least one HIV protein by contacting at least an aliquot of said sample with an immunoreagent specific for detecting the presence of said antibody, said protein being selected from the group consisting of p17, p24 and combinations thereof.

5. The method of any one of claims 1–4 wherein said antibodies are directed against Human Immunodeficiency Virus viral protein p24, and said immunoreagent comprises an antigen immunochemically reactive with said antibodies.

6. The method of any one of claims 1–4 wherein said antibodies are directed against HIV viral protein gp160 and said immunoreagent comprises an antigen immunochemically reactive with said antibodies.

7. The method of any one of claims 1–4 wherein said antibodies are directed against HIV viral protein gp120 and said immunoreagent comprises an antigen immunochemically reactive with said antibodies.

8. The method of any one of claims 1–4 wherein said urine sample is less than one week old.

9. The method of any one of claims 1–4 wherein said immunoreagent comprises an antigen immunochemically reactive with an antibody raised against an HIV viral protein and specific for detecting antibodies to said protein.

10. The method of claim 9 wherein said antibodies are detected using an enzyme-linked immunosorbent assay.

11. The method of claim 9 wherein said antibodies are detected using Western blot.

12. The method of claim 9 said antibodies are detected using immunodiffusion.

13. The method of claim 9 wherein said antibodies are members of the group consisting of antibodies directed against HIV viral protein gp41 (anti-gp41), antibodies directed against HIV viral protein p24 (anti-p24) and combinations thereof and said specific immunoreagent respectively comprises an antigen selected from the group consisting of antigens immunochemically reactive with anti-gp41, antigens immunochemically reactive with anti-p24 and combinations of said antigens.

* * * * *